United States Patent [19]

Isobe

[11] Patent Number: 4,983,823

[45] Date of Patent: Jan. 8, 1991

[54] METHOD FOR DETERMINING INCIDENT ANGLE IN MEASUREMENT OF REFRACTIVE INDEX AND THICKNESS

[75] Inventor: Tami Isobe, Yokohama, Japan

[73] Assignee: Ricoh Company Ltd., Tokyo, Japan

[21] Appl. No.: 467,203

[22] Filed: Jan. 19, 1990

[30] Foreign Application Priority Data

Jan. 20, 1989 [JP] Japan .................................. 1-11037
Jan. 27, 1989 [JP] Japan .................................. 1-18639

[51] Int. Cl.$^5$ .............................................. G02F 1/01
[52] U.S. Cl. ...................................... 250/225; 356/369; 356/382
[58] Field of Search ............... 250/225; 356/364, 366, 356/369, 382

[56] References Cited

U.S. PATENT DOCUMENTS 4,672,196  6/1987  Canino .................................. 250/225
4,725,145  2/1988  Azzam .................................. 356/369

Primary Examiner—David C. Nelms
Attorney, Agent, or Firm—Oblon, Spivak, McClelland, Maier & Neustadt

[57] ABSTRACT

A method for determining a measured incident angle of a monochromatic light for measurement is applied in the measurement of a refractive index and a thickness of a thin film of a single layer formed on a substrate having a known complex refractive index. This method comprises the steps of measuring a first energy reflection ratio of an S-polarized light or a P-polarized light by a measured sample at various angles of incident of the monochromatic light having a certain wavelength used in the measurement; calculating a second energy reflection ratio of the S-polarized light or the P-polarized light when the monochromatic light is incident to the substrate within an incident medium having a certain refractive index, the second energy reflection ratio being calculated by using the complex refractive index and the refractive index of the incident medium as a function of the incident angle; calculating a second angle satisfying an equation in which the first and second reflection ratios are equal to each other with respect to the S-polarized light or the P-polarized light; and setting an angle except for this second angle as the measured incident angle. The other two incident angle determining methods are shown.

14 Claims, 15 Drawing Sheets

DEPENDENCE OF REFLECTION RATIO
ON INCIDENT ANGLE (S-POLARIZED LIGHT)

DEPENDENCE OF REFLECTION RATIO
ON INCIDENT ANGLE (P-POLARIZED LIGHT)

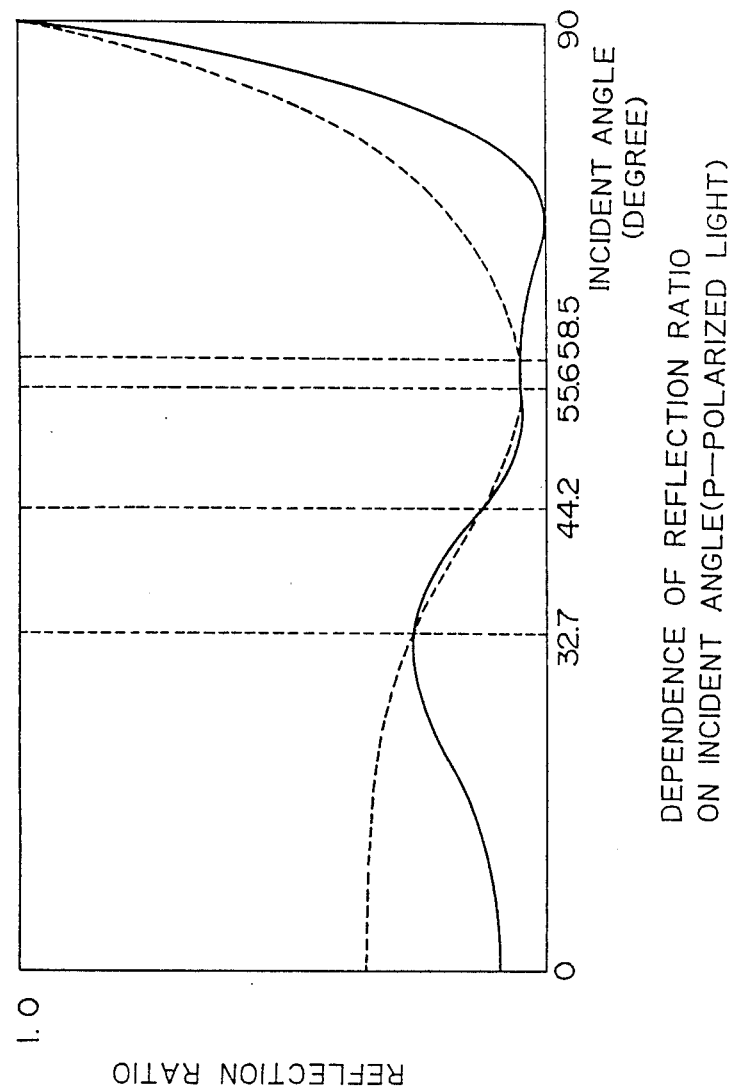

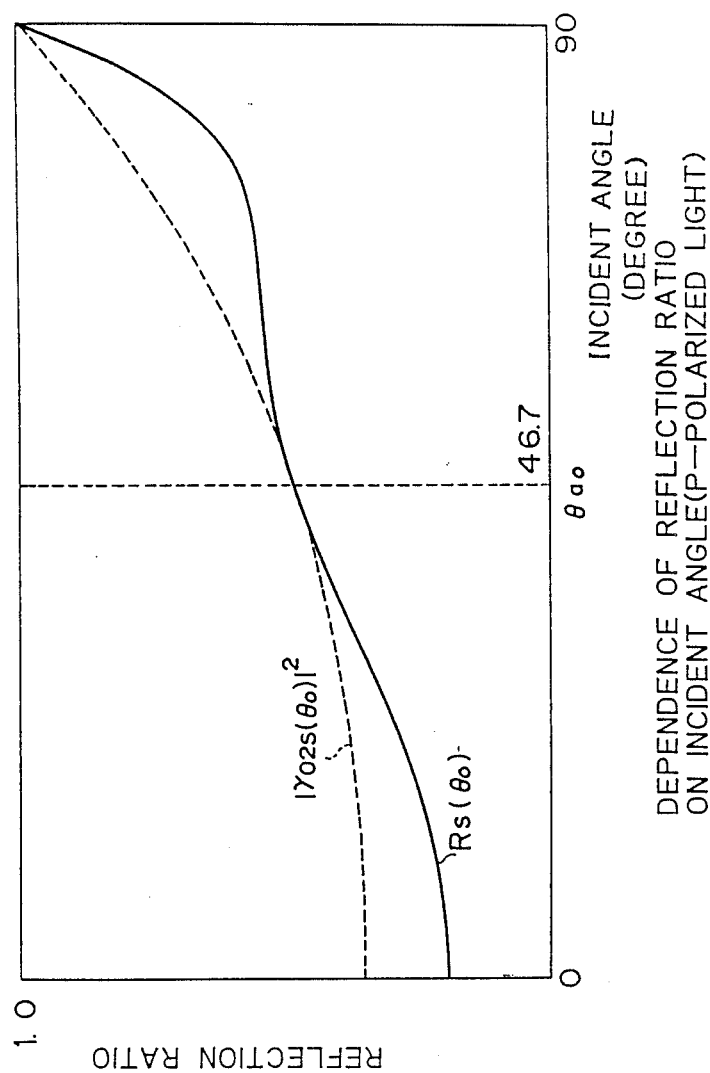

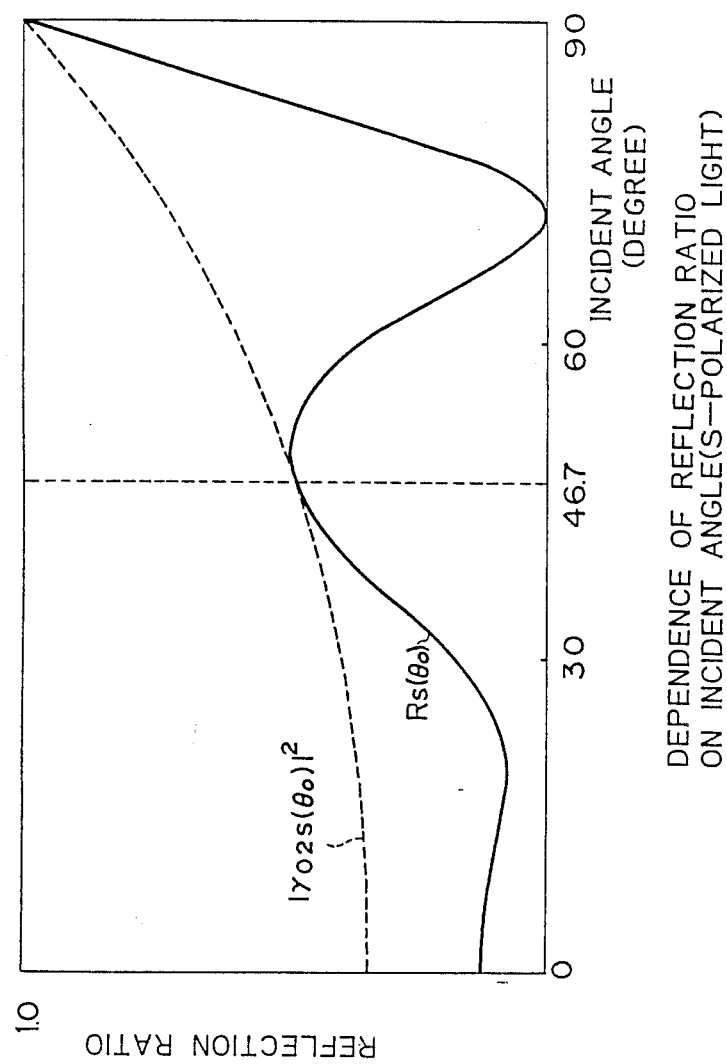

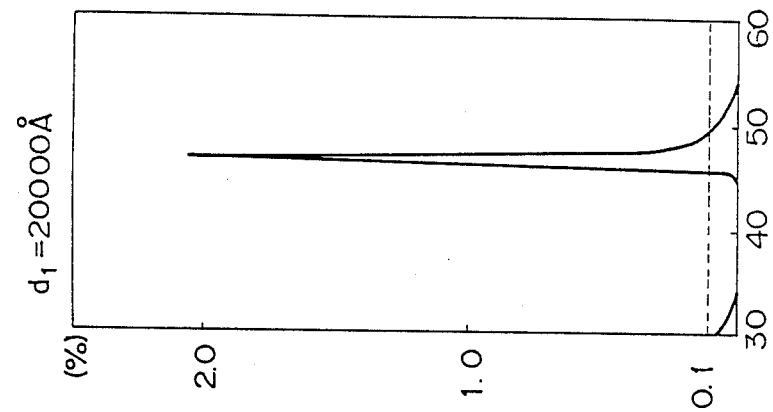
Fig.12  $d_1 = 20000 Å$
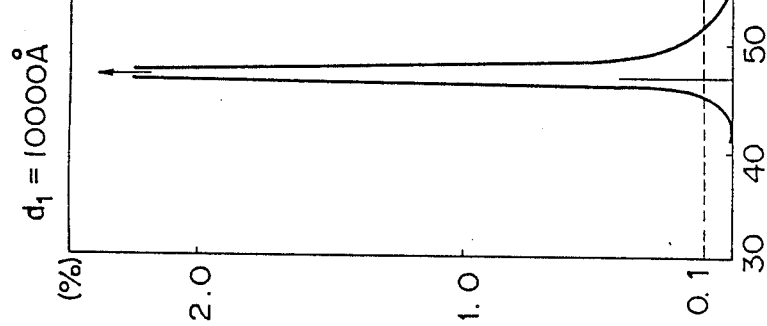
Fig.10  $d_1 = 10000 Å$
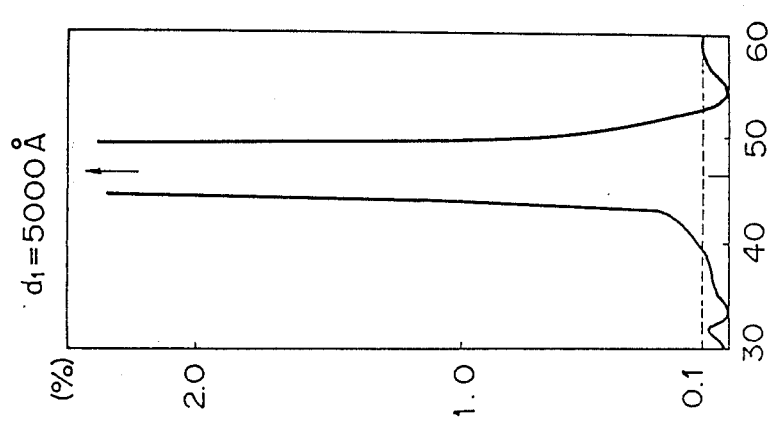
Fig.8  $d_1 = 5000 Å$

DEPENDENCE OF REFLECTION RATIO
ON INCIDENT ANGLE (S-POLARIZED LIGHT)

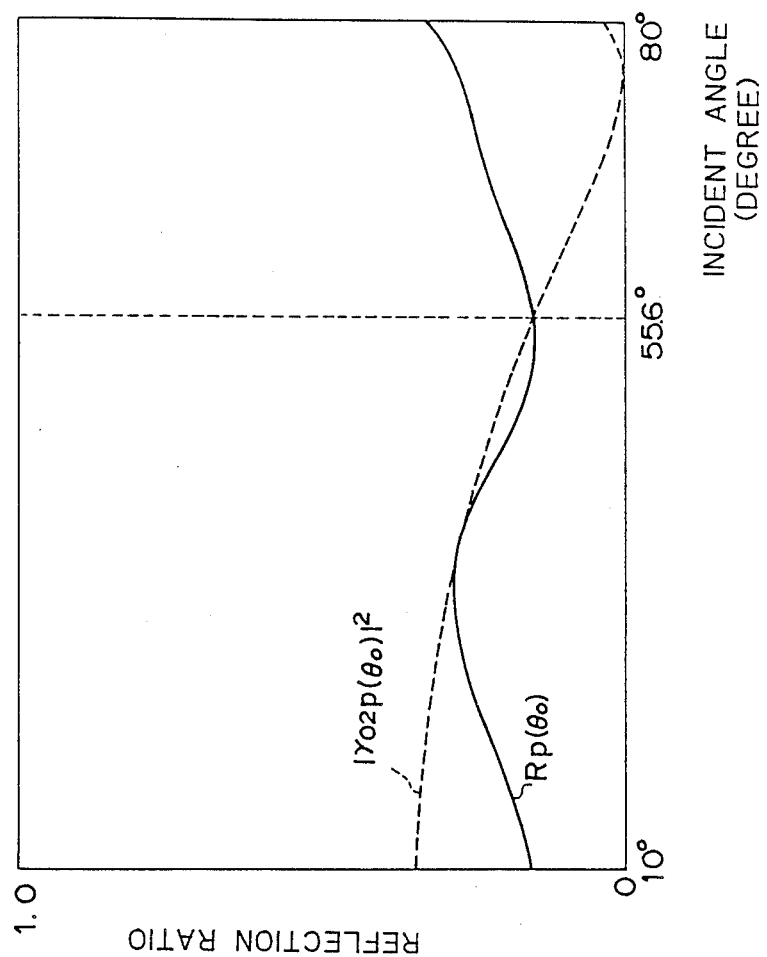

METHOD FOR DETERMINING INCIDENT ANGLE IN MEASUREMENT OF REFRACTIVE INDEX AND THICKNESS

BACKGROUND OF THE INVENTION

1. Field of the Invention

The present invention relates to a method for determining an incident angle in measurement of a refractive index and a thickness.

2. Description of the Related Art

An ellipsometry is known as a method for measuring a refractive index of a thin film and the thickness thereof.

In the ellipsometry, a measuring operation of high accuracy is performed, but there is a case in which the accuracy is greatly reduced with respect to a certain measured film. It is possible to avoid a region reducing the accuracy by changing an incident angle. However, it is impossible to know in advance which incident angle should be selected to obtain a preferable accuracy in measurement. Therefore, it is necessary to calculate a suitable incident angle by a method of trial and error.

Accordingly, the inventor of this application proposed a method of specifying the incident angle at which the accuracy in measurement is deteriorated in advance in Japanese Patent Application No. 62-192396. However, this method is applied to only the measurement of the refractive index and the thickness with respect to a single layer film formed on a substrate having a known complex refractive index. Further, a light used in the measurement is limited to an S-polarized light.

SUMMARY OF THE INVENTION

It is therefore a first object of the present invention to provide a method for determining an incident angle in which the incident angle providing a preferable accuracy in measurement can be easily determined in the execution of the ellipsometry, etc. for measuring the refractive index of a thin film and the thickness thereof.

A second object of the present invention is to provide a method of determining an incident angle in which the incident angle providing an excellent accuracy in measurement can be easily and reliably determined in the execution of the ellipsometry, etc. for measuring the refractive index of a thin film and the thickness thereof.

The above first object of the present invention can be achieved by a method for determining a measured incident angle of a monochromatic light for measurement in the measurement of a refractive index and a thickness of a thin film of a single layer formed on a substrate having a known complex refractive index, the substrate being disposed in an incident medium having a known refractive index, the method comprising the steps of measuring a first reflectance of an S-polarized light or a P-polarized light of a measured sample with the incident medium at various angles of incident of the monochromatic light having a known wavelength used in the measurement; calculating a second reflectance of the S-polarized light of the P-polarized light when the monochromatic light is incident to the substrate within the incident medium the second reflectance being calculated by using the complex refractive index of the substrate and the refractive index of the incident medium as a function of the incident angle; calculating a first angle satisfying an equation in which the first and second reflectance are equal to each other with respect to the S-polarized light or the P-polarized light; and setting a second angle except for this first angle as the measured incident angle.

The present invention also resides in a method for determining a measured incident angle of a monochromatic light for measurement in the measurement of a refractive index and a thickness of a thin film formed on a base body which is composed of the thin film of more than one layer having known refractive index and thickness and stacked on a substrate having a known complex refractive index, the base body being disposed in an incident medium having a known refractive index, the method comprising the steps of measuring first reflectances of an S-polarized light and a P-polarized light of a measured sample within the incident medium at various angles of incident of the monochromatic light having a known wavelength used in the measurement; calculating second reflectances of the S-polarized light and the P-polarized light when the monochromatic light is incident to the base body within the incident medium, the second reflectance being calculated as a function of the incident angle by using the complex refractive index of the substrate, the refractive index of the incident medium and the known refractive index and thickness of each thin film of the base body; calculating a first angle satisfying equations in which the first and second reflectances are equal to each other with respect ot the S-polarized light and the P-polarized light; and setting a second angle except for this second angle as the measured incident angle.

The above second object of the present invention can be achieved by a method for determining a measured incident angle of a monochromatic light for measurement in the measurement of a refractive index and a thickness of a thin film of a single layer formed on a substrate having a known complex refractive index, the substrate being disposed in an incident medium having a known refractive index, the method comprising the steps of measuring a first reflectance of a P-polarized light of a measured sample within the incident medium at various angles to incident of the monochromatic light having a known wavelength used in the measurement; calculating a second reflectance of the P-polarized light when the monochromatic light is incident to the substrate within the incident medium the second reflectance being calculated by using the complex refractive index of the substrate and the refractive index of the incident medium as a function of the incident angle; calculating a first angle satisfying an equation in which the first and second reflectances are equal to each other with respect to the P-polarized light; calculating from the values of the first angle a second angle satisfying a predetermined inequality with respect to a third angle and a fourth angle, the third being smaller than the first angle and proximate to the first angle, the fourth angle being greater than the first angle and proximate to the first angle; and setting the second angle or an angle proximate thereto as the measured incident angle.

Further objects and advantages of the present invention will be apparent from the following description of the preferred embodiments of the present invention as illustrated in the accompanying drawings.

BRIEF DESCRIPTION OF THE DRAWINGS

FIGS. 5 and 6 are graphs for explaining the incident angle determining method in the second embodiment of the present invention;

FIGS. 7, 8, 9, 10, 11 and 12 are graphs for explaining the relation between a measured incident angle and the accuracy in measurement of a refractive index;

FIGS. 18, 19 and 20 are graphs for explaining the concrete embodiments of the present invention.

DESCRIPTION OF THE PREFERRED EMBODIMENTS

Figure 1:
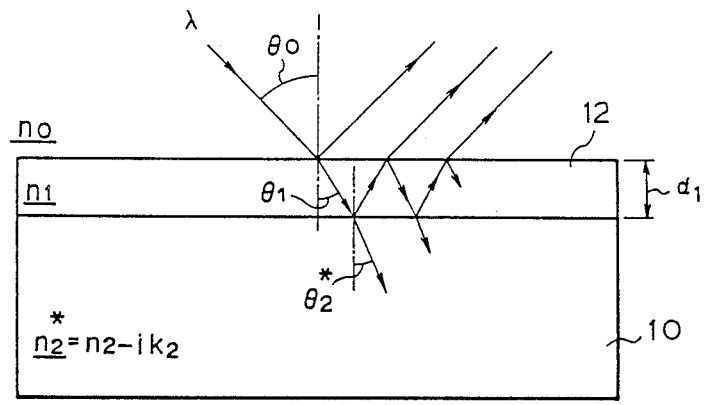
FIG. 1 is a view for explaining a method for determining an incident angle in accordance with a first embodiment of the present invention.

The preferred embodiments of a method for determining an incident angle in measurement of the refractive index of a film and the thickness thereof in the present invention will next be described in detail with reference to the accompanying drawings.

In the following description, three kinds of the incident angle determining methods are proposed.

The method of a first embodiment is a method for determining a measured incident angle of a monochromatic light for measurement in the measurement of a refractive index and a thickness of a thin film of a single layer formed on a substrate having a known complex refractive index $n^*_2 = n_2 - ik_2$. The feature of this method are as follows.

A reflectance $Rs(\theta_0)$ or $Rp(\theta_0)$ of an S-polarized light or a P-polarized light by a measured sample is measured with respect to various values of an incident angle $\theta_0$ of the monochromatic light having a wavelength $\lambda$ used in the measurement.

A reflectance $|r_{02S}(\theta_0)|^2$ or $|r_{02P}(\theta_0)|^2$ or the S-polarized light or the P-polarized light is calculated when the monochromatic light is incident to the substrate within an incident medium having a refractive index $n_0$. This energy reflection ratio $|r_{02S}(\theta_0)|^2$ or $|r_{02P}(\theta_0)|^2$ is calculated by using the refractive indexes $n^*_2$ and $n_0$ as a function of the incident angle $\theta_0$;

An angle $\theta_{a0}$ satisfying the following equation, $$Rs(\theta_0) = |r_{02S}(\theta_0)|^2,$$

or $$Rp(\theta_0) = |r_{02P}(\theta_0)|^2$$

is then calculated.

An angle except for this angle $\theta_{a0}$ is set as the measured incident angle.

The method of a second embodiment is a method for determining a measured incident angle of a monochromatic light for measurement in the measurement of a refractive index and a thickness of a thin film formed on a base body which is composed of the thin film of more than one layer having known refractive index and film thickness and stacked on a substrate having a known complex refractive index $n^*_s = n_s - ik_s$. This method has the following features.

Reflectances $Rs(\theta_0)$ and $Rp(\theta_0)$ of an S-polarized light and a P-polarized light by a measured sample are respectively measured with respect to various values of an incident angle $\theta_0$ of the monochromatic light having a wavelength $\lambda$ used in the measurement.

Reflectances $R_{SbS}(\theta_0)$ and $R_{SbP}(\theta_0)$ of the S-polarized light and the P-polarized light are respectively calculated when the monochromatic light is incident to the base body within an incident medium having a refractive index $n_0$. The reflectances $R_{SbS}(\theta_0)$ and $R_{SbP}(\theta_0)$ are calculated as a function of the incident angle $\theta_0$ by using the refractive indexes $n^*_s$ and $n_0$ and the known refractive index and thickness of each thin film of the base body. An angle $\theta_{a0}$ satisfying both the following equations, $$Rs(\theta_0) = R_{SbS}(\theta_0),$$

and $$Rp(\theta_0) = R_{SbP}(\theta_0)$$

is then calculated.

An angle except for this angle $\theta_{a0}$ is set as the measured incident angle.

As mentioned above, the method of the first embodiment is a method for determining a measured incident angle in the measurement of the refractive index and the thickness of the thin film of a single layer formed on the substrate having the known complex refractive index. The measured incident angle is an angle for making the monochromatic light incident to the measured sample so as to measure the refractive index and the thickness. The monochromatic light having the same wavelength as that used in the measurement is used in the determination of the measured incident angle. In this case, any one of the S-polarized light and the P-polarized light may be used.

The method of the second embodiment is a method for determining the measured incident angle in the measurement of the refractive index and the thickness of the thin film formed on the base body. The base body is constructed by forming the thin film having known refractive index and thickness in the shape of more than one layer on the substrate having the known complex refractive index. Accordingly, in the method of the second embodiment, a plurality of thin films are formed on the substrate and the refractive index and the thickness are measured with respect to an uppermost thin film within the plural thin films on the substrate.

In the method of the second embodiment, the monochromatic lights of the S-polarized light and the P-polarized light are used to determine the measured incident angle as mentioned above.

As the method for measuring the refractive index of the thin film and the film thickness, there is a method (which is briefly called PRETTI method in the following description) proposed by the inventor of this application in Japanese Patent Application No. 62-148742 in addition to the above-mentioned ellipsometry. The present invention can also be applied as a method for determining the incident angle in this PRETTI method in addition to the ellipsometry.

The principle of an incident angle determining method in the first embodiment of the present invention will first be described with reference to FIG. 1.

In FIG. 1, reference numerals 10 and 12 respectively designate a substrate and a transparent thin film. The substrate 10 has a known complex refractive index $n^*_2 = n_2 + ik_2$. A refractive index $n_1$ and a thickness $d_1$ of the thin film 12 are objects to be measured and are unknown. Reference numeral $n_0$ designates a refractive index of an incident medium. It is possible to set $n_0 = 1$ since the incident medium is generally air.

The angles of refraction within the thin film 12 and the substrate 10 are respectively set to $\theta_1$ and $\theta_2$ as shown in FIG. 1 when a monochromatic light having a wavelength $\lambda$ is incident onto the thin film 12 with an incident angle $\theta_0$.

In the following calculation, by using the following formulas, $$\epsilon_2 = n_2^2 - k_2^2, \gamma_2 = 2n_2 k_2,$$

$$2u_2^2 = \epsilon_2 - n_0^2 \sin^2 \theta_0 + \{(\epsilon_2 - n_0^2 \sin^2 \theta)^2 + \gamma_2^2\}^{\frac{1}{2}}$$

$$2v_2^2 = -(\epsilon_2 - n_0^2 \sin^2 \theta_0) + \{(\epsilon_2 - n_0^2 \sin^2 \theta_0)^2 + \gamma_2^2\}^{\frac{1}{2}}$$

$n_2^{*2}$ and $n_2^* \cos \theta_2$ are rewritten as follows.

$$n_2^{*2} = \epsilon_2 - i\gamma_2, n_2 \cos \theta_2 = u_2 + iv_2$$

When the monochromatic light is irradiated onto the thin film 12 as mentioned above, complex amplitude reflectance $r_P$ and $r_S$ of a P-polarized light and an S-polarized light are respectively represented as follows.

$$r_P = \{r_{01P} + r_{12P} \exp(2i\beta_1)\} / \{1 + r_{01P} \cdot r_{12P} \exp(2i\beta_1)\} \quad (1\text{-}1)$$

$$r_S = \{r_{01S} + r_{12S} \exp(2i\beta_1)\} / \{1 + r_{01S} \cdot r_{12S} \exp(2i\beta_1)\} \quad (1\text{-}2)$$

Suffixes P and S respectively designate values with respect to the P-polarized light and the S-polarized light. Reference numerals $r_{01P}$ and $r_{01S}$ respectively designate Fresnel's reflection coefficients with respect to the P-polarized light and the S-polarized light on a boundary face between the incident medium and the thin film 12. Reference numerals $r_{12P}$ and $r_{12S}$ respectively designate Fresnel's reflection coefficients with respect to the P-polarized light and the S-polarized light on a boundary face between the thin film 12 and the substrate 10. Reference numeral $2\beta_1$ designates a change in phase caused during a time interval in which the light goes and returns by one time between front and rear faces of the thin film 12. These values are represented as follows.

$$r_{01P} = (n_1 \cos \theta_0 - n_0 \cos \theta_1)/(n_1 \cos \theta_0 + n_0 \cos \theta_1) \quad (2\text{-}1)$$

$$r_{01S} = (n_0 \cos \theta_0 - n_1 \cos \theta_1)/(n_0 \cos \theta_0 + n_1 \cos \theta_1) \quad (2\text{-}2)$$

$$r_{12P} = (n_2^* \cos \theta_1 - n_1 \cos \theta_2^*)/(n_2^* \cos \theta_1 + n_1 \cos \theta_2^*) \quad (3\text{-}1)$$

$$r_{12S} = (n_1 \cos \theta_1 - n_2^* \cos \theta_2^*)/(n_1 \cos \theta_1 + n_2^* \cos \theta_2^*) \quad (3\text{-}2)$$

$$2\beta_1 = 4\pi d_1 (n_1^2 - \sin^2 \theta_0)^{\frac{1}{2}} / \lambda \quad (4)$$

The $r_{12P}$ and the $r_{12S}$ are generally complex amounts. Therefore, when $r_{12P} = \rho_{12P} \exp(i\Phi_{12P})$ and $r_{12S} = \rho_{12S} \exp(i\Phi_{12S})$, $\rho_{12P}$, $\rho_{12S}$, $\Phi_{12P}$ and $\Phi_{12S}$ are respectively represented as follows.

$$\rho_{12P}^2 = Re^2(r_{12P}) + Im^2(r_{12P}) \quad (5\text{-}1)$$

$$\rho_{12S}^2 = Re^2(r_{12S}) + Im^2(r_{12S}) \quad (5\text{-}1)$$

$$\Phi_{12P} = \tan^{-1}\{Im(r_{12P})/Re(r_{12P})\} \quad (6\text{-}1)$$

$$\Phi_{12S} = \tan^{-1}\{Im(r_{12S})/Re(r_{12S})\} \quad (6\text{-}2)$$

Here, $$Re(r_{12P}) = (p_1 \cdot p_3 + p_2 \cdot p_4)/(p_3^2 + p_4^2)$$

$$Im(r_{12P}) = (p_2 \cdot p_3 - p_1 \cdot p_4)/(p_3^2 + p_4^2)$$

and, $$p_1 = \epsilon_2 l_1 + \gamma_2 v_1 - \epsilon_1 u_2 - \gamma_1 v_2$$

$$p_2 = \epsilon_2 v_1 - \gamma_2 u_1 - \gamma_1 v_2 + \gamma_1 u_2$$

$$p_3 = \epsilon_2 u_1 + \gamma_2 v_1 + \epsilon_1 u_2 + \gamma_1 v_2$$

$$p_2 = \epsilon_2 v_1 - \gamma_2 u_1 + \epsilon_1 v_2 - \gamma_1 u_2$$

Further, $$Re(r_{12S}) = S_1/S_3$$

$$Im(r_{12S}) = S_2/S_3$$

and, $$S_1 = u_1^2 - u_2^2 + v_1^2 - v_2^2$$

$$S_2 = 2(u_2 v_1 - u_1 v_2)$$

$$s_3 = (u_1 + l_2)^2 + (v_1 + v_2)^2$$

Reflectances Rp and Rs are calculated on the basis of the formulas (1-1) and (1-2) and are represented as follows.

$$Rp = \{r_{01P}^2 + \rho_{12P}^2 + 2r_{01P}\rho_{12P}\cos(\Phi_{12P} + 2\beta_1)\}/\{1 + r_{01P}^2 + 2r_{01P}\rho_{12P}\cos(\Phi_{12P} + 2\beta_1)\}$$

$$Rs = \{r_{01S}^2 + \rho_{12S}^2 + 2r_{01S}\rho_{12S}\cos(\Phi_{12S} + 2\beta_1)\}/\{1 + r_{01S}^2\rho_{12S}^2 + 2r_{01S}\rho_{12S}\cos(\Phi_{12S} + 2\beta_1)\}$$

When the incident angle $\theta_0$ is set such that the value $2\beta_1$ in the formula (4) satisfies the following formula (8), $$2\beta_1 = 2m\pi \quad (m = 0, 1, 2, 3 \ldots) \tag{8}$$

the reflectance Rp is represented as follows by substituting the formulas (2-1), (5-1), (6-1) and (8) into the formula (7-1).

$$Rp = \{(n_2^2 + k_2^2)^2 \cos_0^2\theta + n_0^2(u_2^2 + v_2^2) - 2n_0\cos\theta_0(\epsilon_2 u_2 - \gamma_2 v_2)\}/ \tag{9-1}$$
$$\{(n_2^2 + k_2^2)^2 \cos^2\theta_0 + n_0^2(u_2^2 + v_2^2) + 2n_0\cos\theta_0(\epsilon_2 u_2 - \gamma_2 v_2)\}$$

Further, the reflectance Rs is represented as follows by substituting the formulas (2-2), (5-2), (6-2) and (8) into the formula (7-2).

$$Rs = \{(n_0 \cos\theta_o - u_2)^2 + v_2^2\}/\{(n_0 \cos\theta_o + u_2)^2 + v_2^2\} \tag{9-2}$$

These formulas (9-1) and (9-2) do not include the refractive index $n_1$ of the thin film 12 and the thickness $d_1$.

When there is no thin film 12 on the substrate 10 in FIG. 1 and the monochromatic light having the wavelength $\lambda$ is directly incident onto the substrate 10 from the incident medium having the refractive index $n_0$ with the incident angle $\theta_0$, the energy reflection ratios $|r_{02P}|^2$ and $|r_{02S}|^2$ with respect to the P-polarized light and the S-polarized light are respectively represented as follows.

$$|r_{02P}|^2 = |(n_1 \cos\theta_0 - n_0\cos\theta_1)/(n_1\cos\theta_0 + n_0\cos\theta_1)|^2 \tag{10-1}$$
$$= \{(n_2^2 + k_2^2)^2 \cos_0^2\theta + n_0^2(u_2^2 + v_2^2) - 2n_0\cos\theta_0(\epsilon_2 u_2 - \gamma_2 v_2)\}/$$
$$\{(n_2^2 + k_2^2)^2 \cos^2\theta_0 + n_0^2(u_2^2 + v_2^2) + 2n_0\cos\theta_0(\epsilon_2 u_2 - \gamma_2 v_2)\}$$

$$|r_{02S}|^2 = |(n_0\cos\theta_0 - n_1\cos\theta_1)/(n_0\cos\theta_0 + n_1\cos\theta_1)|^2 \tag{10-2}$$
$$= \{(n_0\cos\theta_0 - u_2)^2 + v_2^2\}/\{(n_0\cos\theta_0 + u_2)^2 + v_2^2\}$$

These values are respectively equal to the Rp and the Rs of the formulas (9-1) and (9-2).

These results mean that, when the monochromatic light is incident onto the thin film 12 with the incident angle $\theta_0$ satisfying the formula (8), the reflectances Rp and Rs do not include any information about the refractive index and the thickness of the thin film 12, and are equal to those in the case of only the substrate 10 provided by the above formulas (10-1) and (10-2) as if there is no thin film 12 on the substrate 10. Accordingly, when the light is incident onto the thin film 12 with such a special incident angle, it is impossible in principle to know the refractive index and the thickness of the thin film 12 even when the reflectances are measured.

Such a special incident angle, i.e., the incident angle satisfying the formula (8) is called a singular incident angle in the following description and is represented as $\theta_{a0}$.

Accordingly, when the refractive index and the thickness of the thin film 12 are measured by the ellipsometry, the PRETTI method, etc., it is sufficient to use the incident angle except for the above singular incident angle as a measured incident angle.

The singular incident angle is known as follows. Namely, as mentioned above, with respect to the singular incident angle, the following formula (11-1), $$Rp = |r_{02P}|^2 \tag{11-1}$$

is formed with respect to the P-polarized light, and the following formula (11-2), $$Rs = |r_{02S}|^2 \tag{11-2}$$

is formed with respect to the S-polarized light. The amounts on the left-hand sides of these formulas (11-1) and (11-2) can be known by really irradiating the light onto the thin film 12 and measuring the reflectance thereof. On the other hand, with respect to the amounts on the right-hand sides of these formulas, the complex refractive index of the substrate 10 and the refractive index of the incident medium are known so that the above amounts on the right-hand sides can be calculated by giving the incident angle and performing a calculation according to the formulas (10-1) and (10-2).

When the refractive index and the thickness of the thin film of a single layer formed on the substrate having the known complex refractive index $n*_2 = n_2 - ik_2$ are measured, the reflectance $Rs(\theta_0)$ or $Rp(\theta_0)$ of the S-polarized light or the P-polarized light by a measured sample is measured with respect to various values of the incident angle $\theta_0$ of the monochromatic light having the wavelength $\lambda$ used in the measurement. On the other hand, when the above monochromatic light is incident onto the above substrate within the incident medium having the refractive index $n_0$, the energy reflection ratio $|r_{02S}(\theta_0)|^2$ or $|r_{02P}(\theta_0)|^2$ of the S-polarized light or the P-polarized light is calculated by using the above $n*_2$ and $n_0$ as a function of the incident angle $\theta_0$. Then, the singular incident angle $\theta_{a0}$ satisfying the following equation, $$Rs(\theta_o) = |r_{02S}(\theta_o)|^2$$

or $$Rp(\theta_o) = |r_{02P}(\theta_o)|^2$$

is calculated and it is sufficient to set an angle except for this angle $\theta_{a0}$ as a measured incident angle.

As can be seen from the above description, any one of the P-polarized light and the S-polarized light can be used when the method of the first embodiment is executed. However, in the case of the P-polarized light, the above equation (11-1) is also formed even when the incident angle becomes the Brewster angle on the boundary face between the incident medium and the thin film in addition to the case in which there exists a Brewster angle and the formula (8) is satisfied, i.e., even when $|r_{01P}|^2=0$. In such a case, there is a case in which it is difficult to find the singular incident angle. In consideration of this point, it is preferable to use the S-polarized light.

The incident angle determining method in a second embodiment of the present invention will next be described with reference to FIG. 4.

Figure 4:
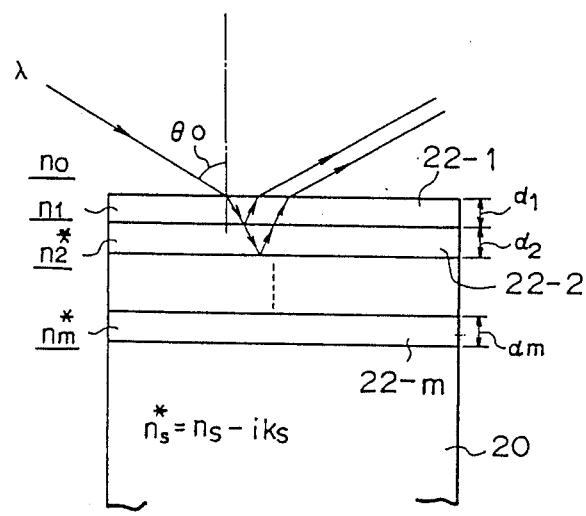
FIG. 4 is a view for explaining the method for determining an incident angle in accordance with a second embodiment of the present invention.

In FIG. 4, thin films 22-1, 22-2, ..., 22-m of m ($\geq 2$) layers are formed on a substrate 20. The thin film 22-1 is a thin film of an uppermost layer and the thin film 22-m is a thin film directly formed on the substrate 20.

Similar to the case of FIG. 1, the refractive index of an incident medium is set to $n_0$. The refractive indexes of the thin films 22-1 to 22-m are sequentially set to $n_1$, $n^*_2$, $n^*_3$, ..., $n^*_m$ and the film thicknesses thereof are sequentially set to $d_1$, $d_2$, ..., $d_m$ as shown in FIG. 4. The thin film 22-1 is transparent and the refractive indexes of the thin films 22-2 to 22-m are complex refractive indexes. Further, the complex refractive index of the substrate 20 is set to $n^*_s = n_s - ik_s$. The complex refractive indexes $n^*_2, n^*_3, ..., n^*_m$ and $n^*_s$ are known and the film thicknesses $d_2, d_3, ..., d_m$ are also known. The refractive index $n_1$ and the thickness $d_1$ of the thin film 22-1 are objects to be measured and are unknown. Accordingly, the substrate 20 and the thin films 22-2 to 22-m constitute a base body and the thin film 22-1 is formed on this base body.

As shown in FIG. 4, when a monochromatic light having a wavelength $\lambda$ is incident onto the thin films of such plural layers with the incident angle $\theta_0$, complex amplitude reflectance $r_P$ and $r_S$ of the P-polarized right and the S-polarized light can be represented as follows.

$$r_r = \{r_{01P} + r'_P \exp(2i\beta_1)\}/\{1 + r_{01P} r'_P \exp(2i\beta_1)\} \quad (12\text{-}1)$$

$$r_s = \{r_{01S} + r'_S \exp(2i\beta_1)\}/\{1 + r_{01S} r'_S \exp(2i\beta_1)\} \quad (12\text{-}2)$$

Here, reference numerals $r_{01P}$ and $r_{01S}$ respectively designate amplitude reflectance of the P-polarized light and the S-polarized light on a boundary face between the incident medium and the thin film 22-1. Reference numerals $r'_P$ and $r'_S$ respectively designate the amplitude reflectance when the above monochromatic light is incident onto the base body within the incident medium having the same refractive index as that of the thin film 22-1. Further, similar to the case of the formula (4), reference numeral $2\beta_1$ designates a change in phase caused during a time interval in which the light goes and returns between front and rear faces of the thin film 22-1.

When the formulas (12-1) and (12-2) are compared with the formulas (1-1) and (1-2) with respect to the amplitude reflectance in the case in which the plural thin films are formed on the substrate 20, the formulas (12-1) and (12-2) are formulas provided by replacing the $r_{12P}$ and the $r_{12S}$ by $r'_P$ and $r'_S$ in the formulas (1-1) and (1-2).

Accordingly, in the case of the incident angle satisfying the above-mentioned formula (8), i.e., the singular incident angle $\theta_{a0}$, the refractive index of the thin film 22-1 and the thickness thereof are canceled from the formulas representing the reflectance so that there are no refractive index and film thickness in these formulas. Thus, the following equations (13-1) and (13-2) are formed.

$$R_P = R_{SbP} \quad (13\text{-}1)$$

$$R_S = R_{SbS} \quad (13\text{-}2)$$

Here, reference numerals $R_{SbP}$ and $R_{SbS}$ respectively designate the reflectance ratios of the P-polarized light and the S-polarized light when the light is incident onto the base body, i.e., a remaining portion except for the uppermost layer thin film with the incident angle $\theta_0$.

Accordingly, in the incident angle determining method in the second embodiment of the present invention, the thin film composed of more than one layer and having the known refractive index and film thickness is stacked on the substrate having the known complex refractive index $n^*_s = n_s - ik_s'$, thereby forming the base body. When the refractive index and the thickness of the thin film formed on the base body are measured, the reflectances $R_s(\theta_0)$ and $R_p(\theta_0)$ of the S-polarized light and the P-polarized light by a measured sample are measured at various angles $\theta_0$ of incident of the monochromatic light having the wavelength $\lambda$ and used in the measurement, thereby calculating the left-hand sides of the equations (13-1) and (13-2). On the other hand, when the above monochromatic light is incident onto the above base body within the incident medium having the refractive index $n_0$, the reflectance $R_{SbS}(\theta_0)$ and $R_{SbP}(\theta_0)$ of the S-polarized light and the P-polarized light are calculated as a function of the incident angle $\theta_0$ by using the above $n^*_s$ and $n_0$ and the known refractive index and thickness of each thin film in the base body, thereby calculating the right-hand sides of the equations (13-1) and (13-2).

Then, the angle $\theta_{a0}$ satisfying both the equations (13-1) and (13-2) is calculated and it is sufficient to determine an angle except for this singular incident angle $\theta_{a0}$ as the measured incident angle.

In the first and second embodiments of the present invention, it is sufficient to automatically perform the above calculations by a computer in which programming is performed in advance.

The concrete embodiments of the present invention will next be described in detail.

Figure 13:
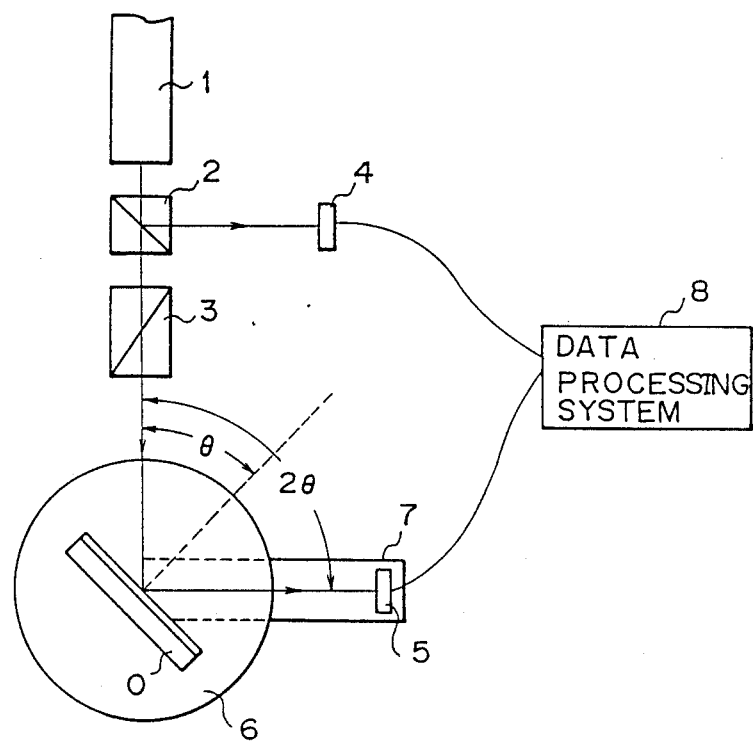
FIG. 13 is a view showing a main portion of an apparatus for executing the incident angle determining method in the embodiments of the present invention.

FIG. 13 schematically shows only a main portion of an apparatus for measuring the refractive index of a thin film and the thickness thereof by using the PRETTI method.

A light source 1 is composed of a He-Ne laser having a wavelength 6328 Å. A light emitted from this light source 1 is divided into two light beams by a beam splitter 2 and one of them is guided to a photodetector 4 so as to perform a photoelectric conversion. The other of the divided light beams is changed by a polarizer 3 to an S-polarized light or an P-polarized light and is incident to a measured sample 0.

The sample 0 is arranged on a turntable 6 rotated by an arm 7. When the arm 7 is rotated by an angle $\theta$, the turntable 6 is rotated by an angle $2\theta$. A photodetector 5 is fixed to an end portion of the arm 7 so as to perform a photoelectric conversion with respect to a light reflected by the sample. By such a construction, it is possible to measure an energy reflectance with respect to an arbitrary incident angle $\theta$ ($0 \leq \theta \leq 90$ degrees) to the sample 0.

Outputs of the photodetectors 4 and 5 are inputted to a data processing system 8 including a computer and become objects to be processed by this processing system 8.

A light quantity ratio of the incident light and the light incident to the photodetector 4 is measured and is inputted to the data processing system 8 in advance.

Embodiments 1 and 2 by simulation will next be described respectively with respect to the incident angle determining method of the first and second embodiments of the present invention so as to easily understand the present invention. Finally, Embodiment 3 with respect to the incident angle determining method in the first embodiment of the present invention will be further described.

EMBODIMENT 1

First Embodiment of the Present Invention

It is assumed that the substrate 10 in FIG. 1 is constructed by an Si substrate having $n^*_2 = 3.858 - 0.018i$ and the thin film 12 on this substrate has the refractive index $n_1 = 1.460$ and the film thickness $d_1 = 6328$ Å. In a situation in which the present invention is really applied, the above $n_1$ and $d_1$ are objects to be measured and are unknown amounts, and the method of the present invention is executed to specify the incident angle for these objects to be measured. However, here, the above unknown amounts are set as known amounts and the method for determining the measured incident angle in the present invention will be described by simulation. Further, the incident medium is set to air and is therefore set to have the $n_0 = 1$.

Figure 2:
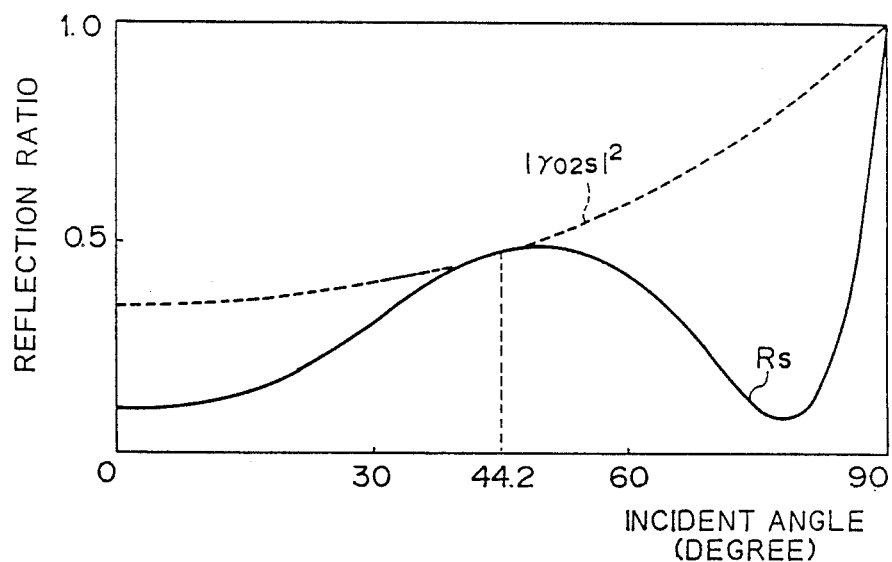
FIGS. 2 and 3 are graphs for explaining the incident angle determining method in the first embodiment of the present invention.

When the laser light beam having the wavelength 6328 Å is incident onto the thin film 12 and this incident angle is continuously changed from 0 to 90 degrees, the reflectance Rs of the S-polarized light is calculated as a function of the incident angle in accordance with the formula (7-2) and is shown by a solid line in FIG. 2. This reflectance Rs is provided as a really measured value when the refractive index of the thin film 12 and the film thickness thereof are really measured.

When the above light is directly incident onto the substrate 10 within the air layer, the reflectance $|r_{02S}|^2$ of the S-polarized light is calculated as a function of the incident angle in accordance with the formula (10-2) and is shown by a broken line in FIG. 2.

As can be seen from FIG. 2, the singular incident angle for forming $Rs = |r_{02S}|^2$ is 44.2 degrees.

Accordingly, it is sufficient to set the measured incident angle to an angle except for 44.2 degrees.

Figure 3:
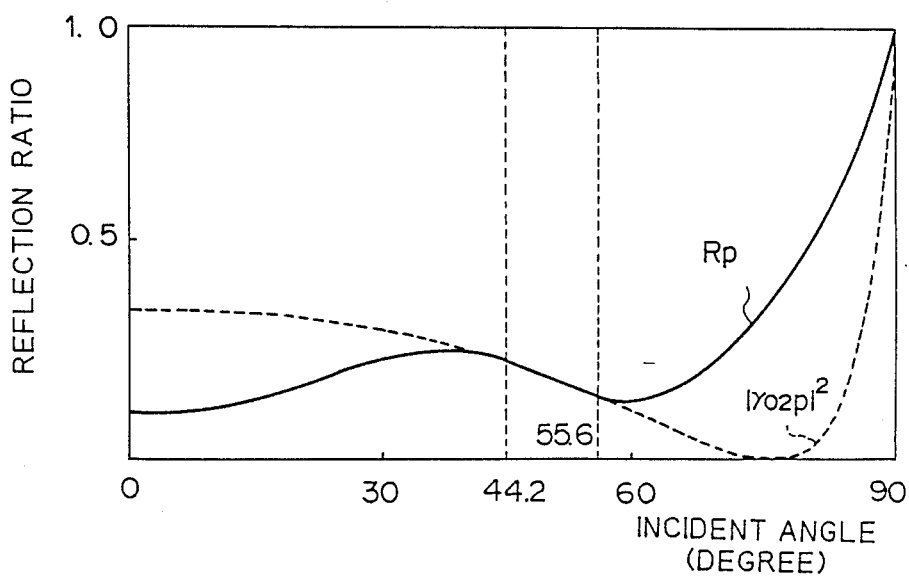

When the same simulation is performed in the case of the P-polarized light instead of the S-polarized light, the reflectance Rp and the $|r_{02P}|^2$ are respectively provided as shown by solid and broken lines in FIG. 3. In this case, the equation $Rs = |r_{02S}|^2$ is formed in the case of the singular incident angle 44.2 degrees as well as the Brewster angle 55.6 degrees. In such a situation, it is difficult to definitely determine the singular incident angle.

EMBODIMENT 2

Second Embodiment of the Present Invention

It is assumed that the substrate 20 in FIG. 4 is constructed by the same Si substrate ($n^*_S = 3.858 - 0.018i$) as that in the Embodiment 1. The base body is constructed by disposing the thin film having the refractive index $n^*_2 = n_2 = 2.000$ and the film thickness 8000 Å on this substrate. It is further assumed that the measured thin film having the refractive index $n_1 = 1.460$ and the film thickness 7400 Å is formed on this base body. In this case, the refractive index $n_0$ is set to be equal to 1.000.

Figure 5:
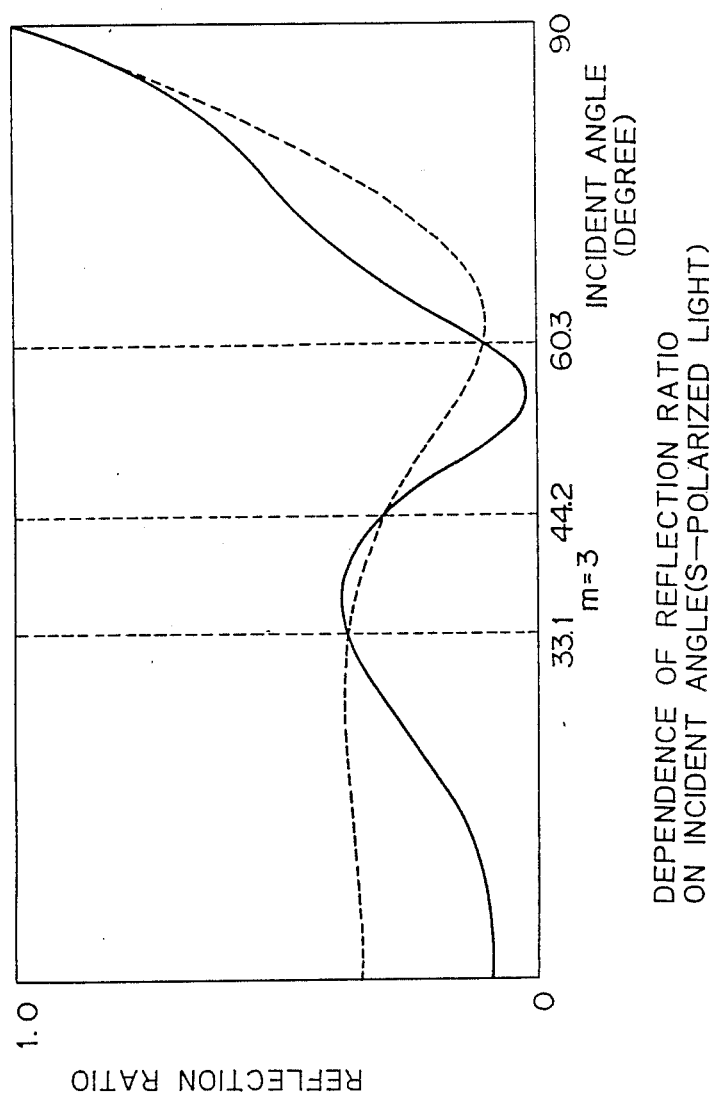

When the laser beam having the wavelength 6328 Å is incident to such a measured sample, the reflectance Rs of the S-polarized light is calculated as a function of the incident angle ranged from 0 to 90 degrees and is provided as shown by a solid line in FIG. 5.

On the other hand, when the above light is directly incident onto the base body in the air, the reflectance $R_{SbS}$ of the S-polarized light is calculated as a function of the incident angle and is provided as shown by a broken line in FIG. 5.

The incident angle forming $Rs = R_{SbS}$ is 33.1 degrees, 44.2 degrees and 60.3 degrees.

When the laser beam having the wavelength 6328 Å is incident to the above measured sample, the reflectance Rp of the P-polarized light is calculated as a function of the incident angle ranged from 0 to 90 degrees and is provided as shown by a solid line in FIG. 6.

Further, when the above light is directly incident onto the base body in the air, the reflectance $R_{SbP}$ of the P-polarized light is calculated as a function of the incident angle and is provided as shown by a broken ling in FIG. 6.

The incident angle forming $Rp = R_{SbP}$ is 32.7 degrees, 44.2 degrees, 55.6 degrees and 58.5 degrees.

Accordingly, the incident angle satisfying both the $Rs = R_{SbS}$ and the $Rp = R_{SbP}$ is 44.2 degrees and this incident angle is provided as a singular incident angle. Accordingly, it is sufficient to determine an angle except for this singular incident angle as the measured incident angle.

As mentioned above, when the present invention is applied to measure the refractive index of the thin film and the film thickness, it is sufficient to specify the singular incident angle and determine an angle except for the singular incident angle as the measured incident angle. The measured incident angle can be freely selected in principle except for the singular incident angle. However, when an angle too close to the singular incident angle is selected as the measured incident angle, no sufficient accuracy can be obtained with respect to the measurement of the refractive index and the film thickness. In the following description, the relation with respect to the difference between the singular incident angle and the measured incident angle, and the accuracy in measurement of the refractive index and the thickness is described as an example when the refractive index of a single layer film is calculated by the PRETTI method.

In the following description, three samples are provided as an example on the basis of the embodiment shown in FIG. 1.

Sample 1: $n_0 = 1.000$, $n_1 = 1.460$, $d_1 = 5000$ Å, $n_2^* = 3.858 - 0.018i$ Sample 2: $n_0 = 1.000$, $n_1 = 1.460$, $d_1 = 10000$ Å, $n_2^* = 3.858 - 0.018i$ Sample 3: $n_0 = 1.000$, $n_1 = 1.460$, $d_1 = 20000$ Å, $n_2^* = 3.858 - 0.018i$ It is assumed that the He-Ne laser beam having the wavelength 6328 Å is used as the incident light.

When this light is incident to the sample 1, the reflectance $Rs(\theta_0)$ with respect to the S-polarized light is calculated as a function of the incident angle ranged from 0 to 90 degrees and is provided as shown by a solid line in FIG. 7. When the light is directly incident onto the substrate, the reflectance $|r_{02S}(\theta_0)|^2$ is calculated and provided as shown by a broken line in FIG. 7.

As can be seen from FIG. 7, the $\theta_0$ is 46.7 degrees when $Rs(\theta_0) = |r_{02S}(\theta_0)|^2$ is formed. Therefore, the reflectance $Rp(\theta_0)$ and $Rs(\theta_0)$ of the P-polarized light and the S-polarized light are calculated when the incident angle is set to an angle close to 46.7 degrees and ranged from 30 to 60 degrees. In the real situation, these amounts are provided as really measured values. By using the results of this calculation, the refractive index of the thin film is calculated by the PRETTI method. FIG. 8 shows the ratio of the difference between the obtained value of the refractive index and a true value 1.460 to the true value.

FIG. 9 shows the $Rs(\theta_0)$ and the $|r_{02S}(\theta_0)|^2$ calculated with respect to the sample 2 by solid and broken lines, respectively.

The reflectance $Rp(\theta_0)$ and $Rs(\theta_0)$ of the P-polarized light and the S-polarized light are calculated when the incident angle is close to the $\theta_0 = 6.7$ degrees and is ranged from 30 to 60 degrees when the $Rs(\theta_0) = |r_{02S}(\theta_0)|^2$ is formed. By using the results of this calculation, the refractive index of the thin film is calculated by the PRETTI method. FIG. 10 shows the ratio of the difference between the obtained value of the refractive index and the true value 1.460 to the true value.

Figure 11:
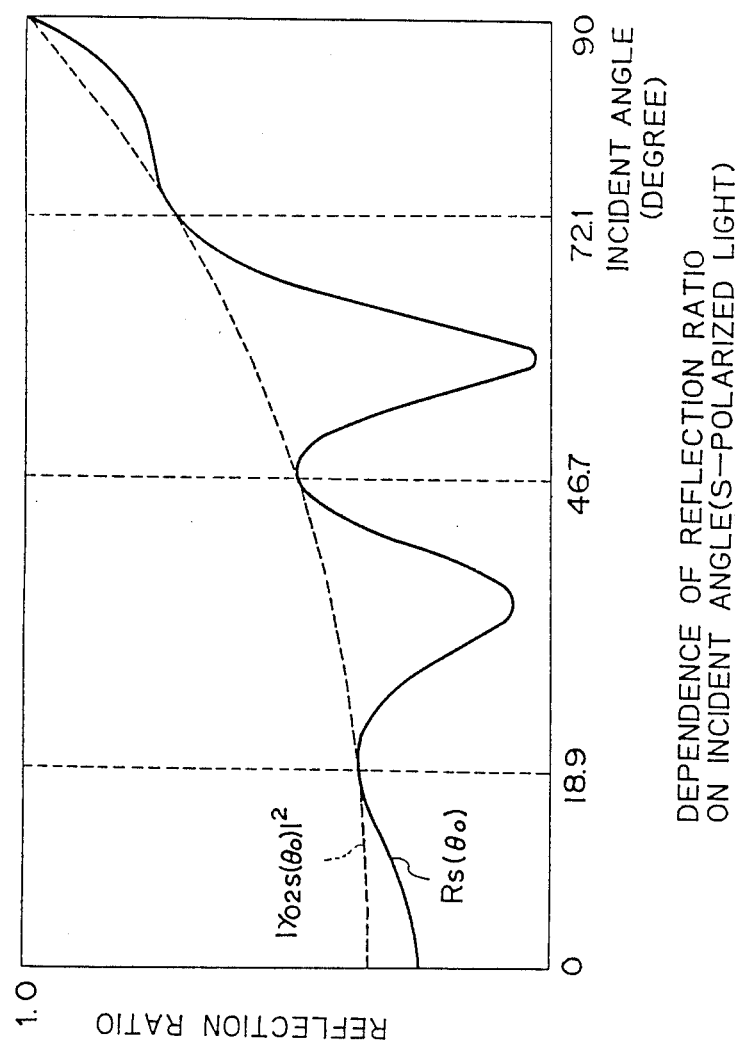

FIG. 11 shows the $Rs(\theta_0)$ and the $|r_{02S}(\theta_0)|^2$ calculated with respect to the sample 3 by solid and broken lines, respectively.

Further, the reflectance $Rp(\theta_0)$ and $Rs(\theta_0)$ of the P-polarized light and the S-polarized light are calculated when the incident angle includes the first two angles of 18.9 degrees, 46.7 degrees and 72.1 degrees as the $\theta_0$ and is ranged from 30 to 60 degrees when the $Rs(\theta_0) = |r_{02S}(\theta_0)|^2$ is formed. By using the results of this calculation, the refractive index of the thin film is calculated by the PRETTI method. FIG. 12 shows the ratio of the difference between the obtained value of the refractive index and the true value 1.460 to the true value.

The value m in the formula (8) is called a degree of the singular incident angle in the following description. This degree providing the singular incident angle 46.7 degrees is provided as m=2 with respect to the sample 1, as m=4 with respect to the sample 2 and as m=8 with respect to the sample 3. In FIGS. 8, 10 and 12, each curve is a curve of a δ-function type diverging at the singular incident angle 46.7 degrees in the case of each sample. The width of a diverging portion is narrowed as the above degree m increases. When the range of the incident angle $\theta_0$ is approximately provided by the following equality and inequality, $$\theta_0 \leq \theta_{a0} - (90/5\,m),\ \theta_0 \geq \theta_{a0} + (90/5\,m)\ \text{(unit of angle: degree)} \quad (14)$$

with respect to the singular incident angle $\theta_{a0}$, the obtained accuracy in refractive index is provided within 0.1%.

Accordingly, after the singular incident angle is provided, it is possible to perform a measurement of high accuracy if the measured incident angle is set in a region of the incident angle satisfying the inequality (14). For example, in the case of the sample 3, the singular incident angle is provided by the degree m=8 so that the incident angle region providing the accuracy in measurement of the refractive index within 0.1% is provided by the following equality and inequality, $$\theta_0 \leq 44.5\ \text{degrees},\ \theta_0 \geq 48.95\ \text{degrees}$$

from the inequality (14). Accordingly, it is sufficient to set the measured incident angle within this region. However, the accuracy is reduced by the influence of the singular incident angle of a different degree in the vicinity of the angles 18.9 degrees and 72.1 degrees. Therefore, it is preferable to set the measured incident angle in a region having no influence of the singular incident angle of another degree in the range provided by the inequality (14).

EMBODIMENT 3

A concrete embodiment will next be described when the refractive index of a single layer film and the thickness thereof are measured.

An Si substrate having a complex refractive index $n^*_2 = 3.858 - 0.018i$ is used as the substrate 10. An $SiO_2$ film as the thin film 12 is disposed by thermal oxidation on this substrate, thereby forming a sample O to be measured. This sample is arranged on the turntable 6 in FIG. 13 and the incident angle $\theta_0$ is continuously changed in a range from 10 to 80 degrees. The photoelectric converting outputs of the photodetectors 4 and 5 are inputted to the data processing system 8 every 0.1 degree with respect to the incident angle. Then, the energy reflection ratio Rs($\theta_0$) of the S-polarized light in the above incident angle region is measured every 0.1 degree with respect to the incident angle. The results of this measurement are shown by a solid line in FIG. 14. A broken line in FIG. 14 shows the results of the reflection ratio $|r_{02S}(\theta_0)|^2$ calculated when the S-polarized light is directly incident onto the substrate at the same incident angle.

Figure 14:
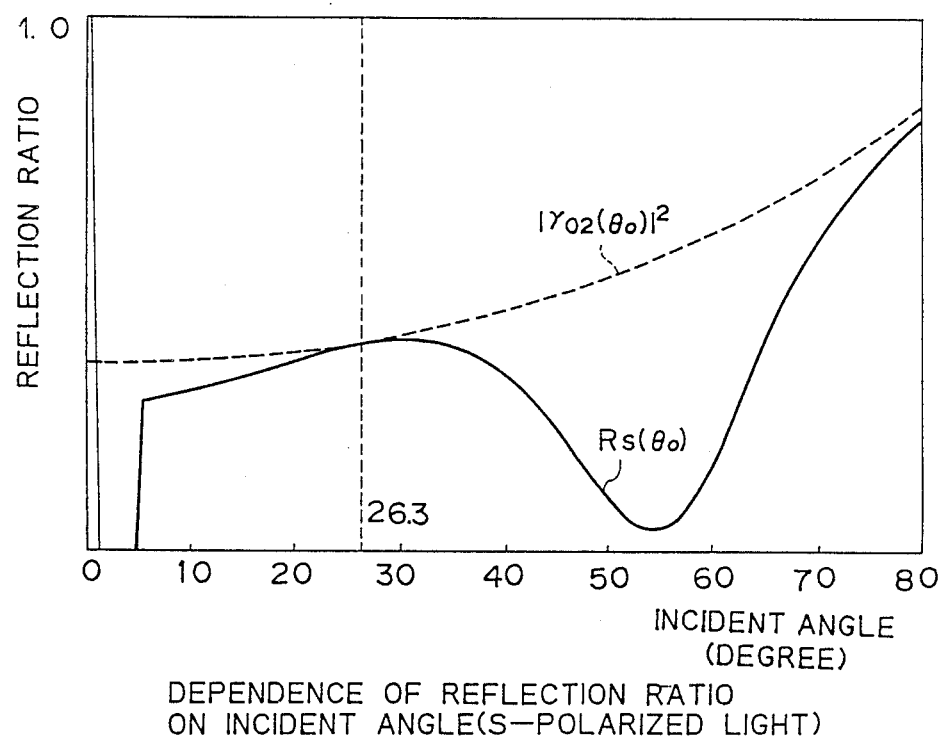
FIGS. 14, 15 and 16 are graphs for explaining the incident angle determining method in the first embodiment of the present invention applied to the concrete measurement of the refractive index and the film thickness.

As can be seen from FIG. 14, the $\theta_0$ is 26.7 degrees when the equation Rs($\theta_0$) = $|r_{02S}(\theta_0)|^2$ is formed. This angle is a singular incident angle. Therefore, the measured incident angle is determined as 50.0 degrees and is set with respect to the sample 0. Next, the reflectances of the S-polarized light and the P-polarized light with respect to this measured incident angle are measured by setting the polarizer 3 and the following results are obtained.

$$Rs(50.0°) = 0.0991452, Rp(50.0°) = 0.127581$$

By using these values, the refractive index of the SiO$_2$ thin film is calculated by the PRETTI method and is obtained as n = 1.459.

Figure 15:
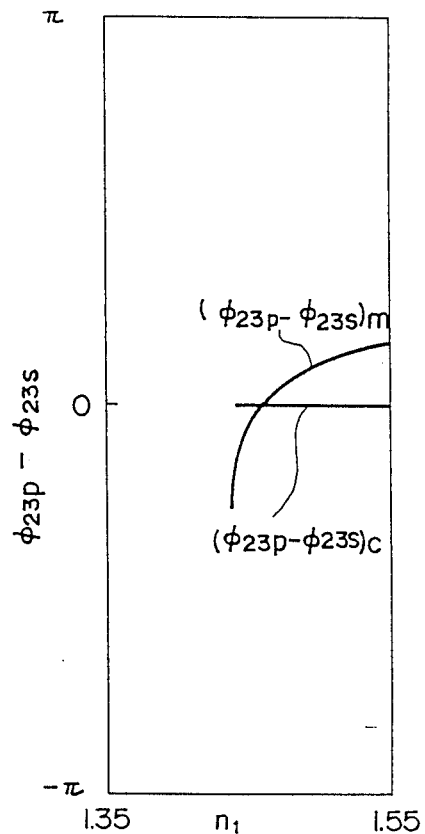

FIG. 15 shows a measured value ($\phi_{23P} - \phi_{23S}$)m and a calculated value ($\phi_{23P} - \phi_{23S}$)c with respect to a value ($\phi_{23P} - \phi_{23S}$) calculated to provide the refractive index. In this figure, the refractive index of the thin film is changed from 1.35 to 1.55.

In the PRETTI method, the accuracy in refractive index is improved as the curves shown by the ($\phi_{23P} - \phi_{23S}$)m and the ($\phi_{23P} - \phi_{23S}$)c clearly cross each other. As can be seen from FIG. 15, both the curves clearly cross each other at $n_1 = 1.459$ so that the obtained accuracy in refractive index is high.

Further, the above measured sample is set to an ellipsometer and the refractive index and the film thickness are measured by the ellipsometry with the incident angle 50.0°. As a result, the refractive index $n_1 = 1.459$ and the thickness $d_1 = 9117$ Å are obtained.

Figure 16:
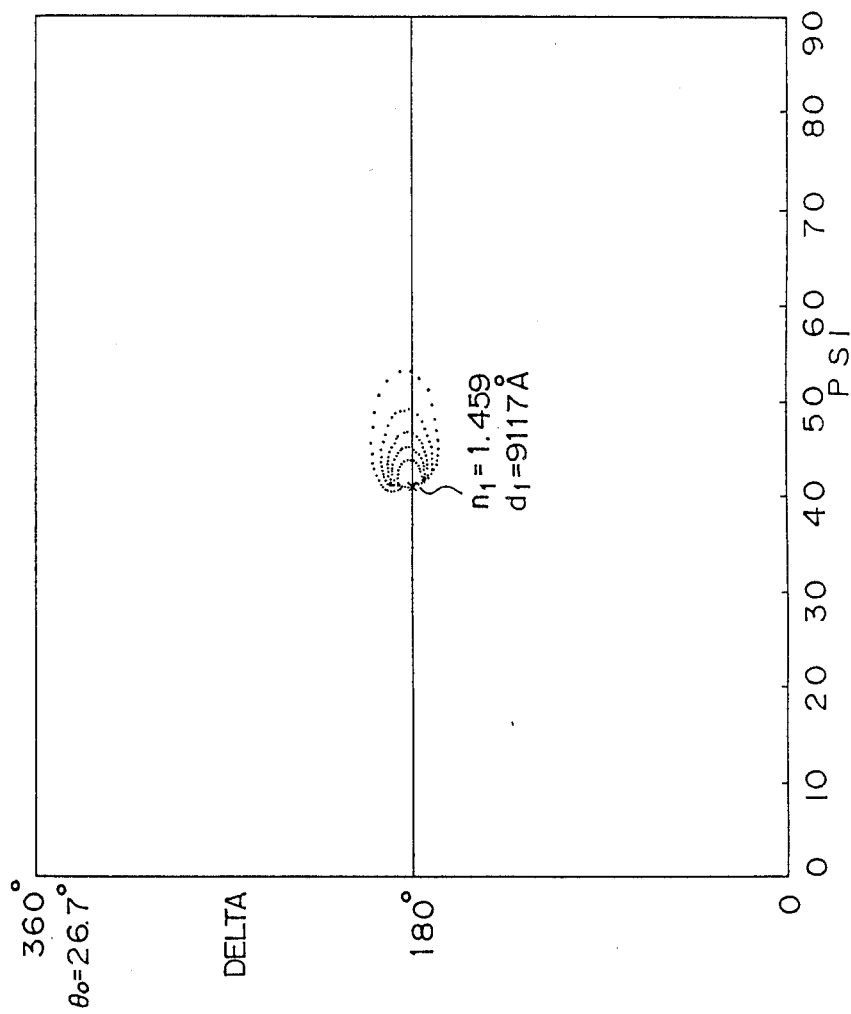

The singular incident angle with respect to this measured sample is 26.7 degrees as mentioned before. FIG. 16 is a psi-delta view of the above measured sample in the ellipsometry. In this figure, the curves having refractive indexes different from each other come into contact with each other at a point shown by a mark x and providing the $n_1 = 1.459$ and the $d_1 = 9117$ Å. At this point, it is very difficult to really determine the refractive index. Accordingly, the refractive index of the thin film and the thickness cannot be determined in principle at the singular incident angle even when the ellipsometry is used.

As mentioned above, the present invention can provide a novel method for determining the incident angle in the measurement of the refractive index of the thin film and the film thickness. Since this method is constructed as above, it is possible to easily and reliably determine a measured incident angle for providing a preferable accuracy in measurement of the refractive index of the thin film and the film thickness.

The incident angle determining method in a third embodiment of the present invention will next be described in detail.

The third embodiment of the present invention is a method for determining a measured incident angle of a monochromatic light for measurement in the measurement of a refractive index and a film thickness of a thin film of a single layer formed on a substrate having a known complex refractive index $n^*_2 = n_2 - ik_2$. This method has the following features.

A reflectance Rp($\theta_0$) of a P-polarized light by a measured sample is measured within an incident medium having a refractive index $n_0$ with respect to various values of an incident angle $\theta_0$ of the monochromatic light having a wavelength $\lambda$ used in the measurement.

A reflectance $|r_{02P}(\theta_0)|^2$ of the P-polarized light is calculated when the monochromatic light is incident to the substrate within the incident medium having the refractive index $n_0$. The reflectance $|r_{02P}(\theta_0)|^2$ is calculated by using the refractive indexes $n^*_2$ and $n_0$ as a function of the incident angle $\theta_0$.

An angle $\theta_B$ satisfying the following equation, $$Rp(\theta_0) = |r_{02P}(\theta_0)|^2$$

is then calculated. From the values of the angle $\theta_B$, an angle $\theta_{0B}$ satisfying the following inequality, $$(Rp(\theta_A) - |r_{02P}(\theta_A)|^2) \times (Rp(\theta_C) - |r_{02P}(\theta_C)|^2) < 0$$

is calculated with respect to angles $\theta_A$ and $\theta_C$ proximate to the angle $\theta_B$ before and after this angle $\theta_B$ where the angle $\theta_A$ is smaller than the angle $\theta_B$ and the angle $\theta_C$ is greater than the angle $\theta_B$. This angle $\theta_{0B}$ or an angle proximate thereto is determined as the measured incident angle.

In this method of the present invention, the monochromatic light of the P-polarized light having the same wavelength as that used in the measurement is used in the determination of the measured incident angle.

The principle of the incident angle determining method in the third embodiment of the present invention will next be described with reference to FIG. 17.

In FIG. 17, reference numerals 110 and 112 respectively designate a substrate and a transparent thin film. The substrate 110 has a known complex refractive index $n^*_2 = n_2 - ik_2$. A refractive index $n_1$ and a thickness $d_1$ of the thin film 112 are objects to be measured and are unknown. Reference numeral $n_0$ designates a refractive index of an incident medium. It is possible to set $n_0 = 1$ since incident medium is generally air.

Figure 17A:
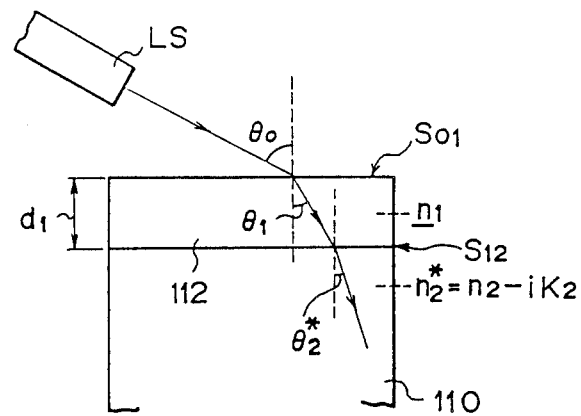
FIGS. 17a and 17b are views for explaining the incident angle determining method in a third embodiment of the present invention.

As shown in FIG. 17a, the angles of refraction within the thin film 112 and the substrate 110 are respectively set to $\theta_1$ and $\theta^*_2$ when a monochromatic light having a wavelength $\lambda$ from a monochromatic light source LS is incident onto the thin film 112 with an incident angle $\theta_0$.

In the following calculation, by using the following formulas, $$\epsilon_2 = n_2^2 - k_2^2, \gamma_2 = 2n_2k_2,$$

$$2u_2^2 = \epsilon_2 - n_0^2\sin^2\theta_0 + \{(\epsilon_2 - n_0^2\sin^2\theta_0)^2 + \gamma_2^2\}^{\frac{1}{2}}$$

$$2v_2{}^2 = -(\epsilon_2 - n_0{}^2\sin^2\theta_0) + \{(\epsilon_2 - n_0{}^2\sin^2\theta_0)^2 + \gamma_2{}^2\}^{\frac{1}{2}}$$

$n_2{}^{*2}$ and $n_2{}^*\cos\theta_2{}^*$ are rewritten as follows.

$$n_2{}^{*2} = \epsilon_2 - i\gamma_2, \quad n_2{}^*\cos\theta_2{}^* = u_2 + iv_2$$

When the monochromatic light is irradiated onto the thin film 112 as mentioned above, a complex amplitude reflection ratio $r_P$ of a P-polarized light is represented by the following formula.

$$r_P = \{r_{01P} + r_{12P}\exp(2i\beta_1)\}/\{1 + r_{01P}r_{12P}\exp(2i\beta_1)\} \quad (15)$$

Reference numeral $r_{01P}$ designates a Fresnel's reflection coefficient with respect to the P-polarized light on a boundary face $S_{01}$ between the incident medium and the thin film 112. Reference numeral $r_{12P}$ designates a Fresnel's reflection coefficient with respect to the P-polarized light on a boundary face $S_{12}$ between the thin film 112 and the substrate 110. Reference numeral $2\beta_1$ designates a change in phase caused during a time interval in which the light goes and returns by one time between front and rear faces of the thin film 112, i.e., between the boundary faces $S_{01}$ and $S_{12}$. These values are represented as follows.

$$r_{01P} = (n_1\cos\theta_0 - n_0\cos\theta_1)/(n_1\cos\theta_0 + n_0\cos\theta_1) \quad (16)$$

$$r_{12P} = (n_2{}^*\cos\theta_1 - n_1\cos\theta_2{}^*)/(n_2{}^*\cos\theta_1 + n_1\cos\theta_2{}^*) \quad (17)$$

$$2\beta_1 = 4\pi d_1(n_1{}^2 - \sin^2\theta_0)^{\frac{1}{2}}/\lambda \quad (18)$$

The $r_{12P}$ is generally a complex amount. Therefore, when $r_{12P} \equiv \rho_{12P}\exp(i\Phi_{12P})$, $\rho_{12P}$ and $\phi_{12P}$ are respectively represented as follows.

$$\rho_{12P}{}^2 = Re^2(r_{12P}) + Im^2(r_{12P}) \quad (19)$$

$$\Phi_{12P} = \tan^{-1}\{Im(r_{12P})/Re(r_{12P})\} \quad (20)$$

Here, $$Re(r_{12P}) = (p_1 \cdot p_3 + p_2 \cdot p_4)/(p_3{}^2 + p_4{}^2)$$

$$Im(r_{12P}) = (p_2 \cdot p_3 - p_1 \cdot p_4)/(p_3{}^2 + p_4{}^2)$$

and, $$p_1 = \epsilon_2 U_1 + \gamma_2 V_1 - \epsilon_1 U_2 - \gamma_1 V_2$$

$$p_2 = \epsilon_2 V_1 - \gamma_2 U_1 - \epsilon_1 V_2 + \gamma_1 U_2$$

$$p_3 = \epsilon_2 U_1 + \gamma_2 V_1 + \epsilon_1 U_2 + \gamma_1 V_2$$

$$p_4 = \epsilon_2 V_1 - \gamma_2 U_1 + \epsilon_2 V_2 - \gamma_1 U_2$$

When the Brewster angle on the boundary face $S_{01}$ between the incident medium and the thin film 112 is set to $\theta_{0B}$, $r_{01P} = 0$ is formed with respect to this Brewster angle $\theta_{0B}$. In the case in which the angle of refraction within the thin film 112 is set to $\theta_{1B}$ when the angle incident onto the thin film 112 is the $\theta_{0B}$, as is well known, the following formulas, $$\tan\theta_{0B} = (n_1/n_0), \quad \theta_{0B} + \theta_{1B} = \pi/2 \quad (21)$$

are formed. In the case in which the angle of refraction within the substrate 110 is set to $\theta^*_{2B}$ when the angle incident onto the thin film 112 is the $\theta_{0B}$, the following formula, $$\begin{aligned}r_{12P} &= [n_2{}^*\cos\{(\pi/2) - \theta_{OB}\} - n_1\cos\theta_{2B}{}^*]/ \\ &\quad [n_2{}^*\cos\{(\pi/2) - \theta_{OB}\} + n_1\cos\theta_{2B}{}^*] \\ &= (n_2{}^*\cos\theta_{OB} - n_0\cos\theta_{2B}{}^*)/ \\ &\quad (n_2{}^*\cos\theta_{OB} + n_0\cos\theta_{2B}{}^*) \\ &= r_{02P}\end{aligned} \quad (22)$$

is formed by substituting the formulas (21) into the formula (17).

Figure 17B:
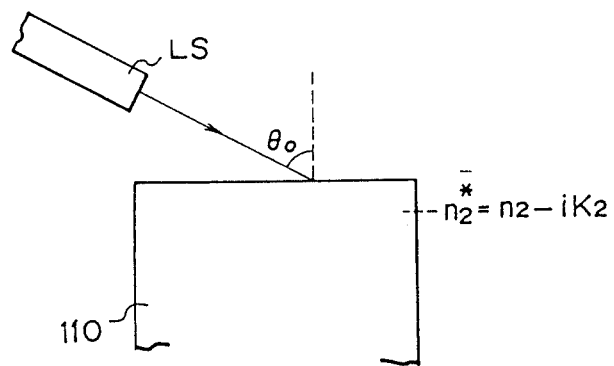

As can be seen from the formula (22), $r_{02P}$ is a Fresnel's reflection coefficient of the P-polarized light when the monochromatic light is directly incident onto the substrate 110 within the incident medium having the refractive index $n_0$. FIG. 17b shows this state in which the monochromatic light is directly incident onto the substrate 110 within the incident medium having the refractive index $n_0$. At this time, the reflection is $|r_{02P}|^2$.

When the monochromatic light is incident onto the thin film 112 with the incident angle $\theta_{0B}$, the energy reflection ratio $Rp(\theta_{0B})(\equiv |r_P|^2)$ of the P-polarized light is provided as follows when the $r_{01P}$ is set to 0 in the formula (15).

$$R_P(\theta_{0B}) = |r_{12P}|^2 \quad (23)$$

Accordingly, when the angle $\theta_0$ incident onto the thin film 112 is the Brewster angle $\theta_{0B}$, the following formula, $$R_P(\theta_{0B}) = |r_{02P}(\theta_{0B})|^2 \quad (24)$$

is formed in accordance with the formulas (22) and (23).

As mentioned above, the $|r_{02P}|^2$ is the reflectance when the monochromatic light of the P-polarized light is directly incident onto the substrate 110 within the incident medium having the refractive index $n_0$. This $|r_{02P}|^2$ can be represented as follows by rewriting the formula (22) using the Snell's law.

$$|r_{02P}|^2 = [(\epsilon_2\cos\theta_0 - n_0 U_2)^2 + (\gamma_2\cos\theta_0 + n_0 V_2)^2] \\ /[(\epsilon_2\cos\theta_0 + n_0 U_2)^2 + (\gamma_2\cos\theta_0 - n_0 V_2)^2] \quad (25)$$

On the right-hand side of this formula (25), the $|r_{02P}|^2$ is a function of $\epsilon_2$, $\gamma_2$, $\theta_0$, $n_0$, $u_2$ and $v_2$, but $\epsilon_2$, $\gamma_2$, $u_2$ and $v_2$ are functions of the complex refractive index $n^*_2$ of the substrate 110 and the incident angle $\theta_0$.

With respect to the substrate 110, the $n^*_2$ is known and the refractive index $n_0$ of the incident medium is also known and is normally 1.0. Accordingly, when these known values are substituted onto the right-hand side of the formula (25), the $|r_{02P}|^2$ can be represented as a function $|r_{02P}(\theta_0)|^2$ of the incident angle $\theta_0$. This function can be provided by only a calculation instead of the real measurement thereof.

On the one hand, the monochromatic light of the P-polarized light having the wavelength λ is incident onto the thin film 112 at various values of the incident angle $\theta_0$ and the energy reflection ratio Rp($\theta_0$) is really measured with the incident angle $\theta_0$ as a parameter. On the other hand, the above $|r_{02P}|^2$ is calculated as a function of the incident angle $\theta_0$ in accordance with the formula (25). Then, the Brewster angle $\theta_{0B}$ is calculated as an angle at which the above reflection ratio and the above $|r_{02P}|^2$ are equal to each other. This angle is a solution of the following equation, $$Rp(\theta_0) = |r_{02P}(\theta_0)|^2 \qquad (26).$$

When the monochromatic light of the P-polarized light is incident onto the thin film 112, the phase in reflection is changed from 0 to π or π to 0 before and after the incident angle $\theta_0$ is the Brewster angle. Since this phase is rapidly changed before and after the Brewster angle, the sensitivity of a phase changing amount with respect to the refractive index of the thin film is high. Accordingly, in a measuring system for providing the refractive index of the thin film by calculating the phase changing amount by reflection such as the ellipsometry and the PRETTI method, it is possible to perform a measuring operation of high accuracy by using the Brewster angle $\theta_{0B}$ on the boundary face between the thin film and the incident medium as a measured incident angle.

The above Brewster angle satisfies the above equation (26), but all the incident angles satisfying this equation (26) are not the Brewster angle. In other words, the Brewster angle cannot necessarily be specified by only the equation Rp($\theta_0$) = $|r_{02P}(\theta_0)|^2$. Accordingly, it is necessary to set a condition for judging the Brewster angle from the incident angles satisfying the above equation (26).

As this judging condition, it is possible to utilize the fact that the functions on the left-hand side and the right-hand side of the equation (26) cross each other at the Brewster angle.

Namely, when the incident angle satisfying the equation Rp($\theta_0$) = $|r_{02P}(\theta_0)|^2$ is generally set to $\theta_B$ and angles $\theta_A$ and $\theta_C$ satisfying the following inequality, $$\theta_A < \theta_B < \theta_C$$

are selected such that these angles are proximate to the $\theta_B$ before and after the $\theta_B$ and the following value, $$(Rp(\theta_A) - |r_{02P}(\theta_A)|^2) \cdot (Rp(\theta_C) - |r_{02P}(\theta_C)|^2)$$

is calculated, the condition in which the $\theta_B$ is the Brewster angle is provided as follows.

$$(Rp(\theta_A) - |r_{02P}(\theta_A)|^2) \cdot (Rp(\theta_C) - |r_{02P}(\theta_C)|^2) < 0 \qquad (27)$$

Accordingly, the Brewster angle $\theta_{0B}$ can be specified as the incident angle satisfying the equation (26) and the inequality (27) so that this angle can be determined as the measured incident angle.

After the Brewster angle is thus provided, the refractive index of the thin film and the thickness are measured by using this angle $\theta_{0B}$ or an angle proximate to this angle as the measured incident angle.

The processing for calculating the right-hand side of the above equation (26), the processing for calculating the angle $\theta_B$ satisfying this equation, and the processing for specifying the angle $\theta_{0B}$ satisfying the inequality (27) from the values of the $\theta_B$ can be executed by using a calculating means such as a computer in which programming of the above-mentioned calculating processings is performed in advance.

An Si substrate having n*₂ = 3.858 − 0.018i is used as the substrate 110 in FIG. 17a and 17b. A film made of SiO₂ as the thin film 112 is formed by thermal oxidation on this substrate, thereby providing a sample O to be measured. As shown in FIG. 13, this measured sample is set on the turntable 6 and the laser beam of the above P-polarized light is incident onto the thin film 112 with the air as an incident medium (n₀ = 1.0). This incident angle is continuously changed in a range from 10 to 80 degrees. The photodetectors 4 and 5 are synchronized in operation to perform a photoelectric conversion every 0.1 degree with respect to the incident angle. The photoelectrically converted results are inputted to the data processing system 8.

FIG. 18 shows the reflectance Rp($\theta_0$) thus measured by a solid line.

A broken line in FIG. 18 shows the results of the energy reflection ratio $|r_{02P}|^2$ of the P-polarized light calculated as a function of the incident angle according to the formula (25) in the case in which the above light is directly incident onto the substrate 110 in the air layer.

As can be seen from FIG. 18, the Brewster angle is 55.6 degrees when the equation (26), i.e., Rp($\theta_0$) = $|r_{02P}(\theta_0)|^2$ is formed and the inequality (27) is formed.

Therefore, the measured incident angle is set as this 55.6 degrees or an angle close to this angle.

The refractive index of the SiO₂ film is provided by the PRETTI method using the measured incident angle 55.6 degrees determined as above and the refractive index n₁ = 1.460 is thus obtained.

Figure 19:
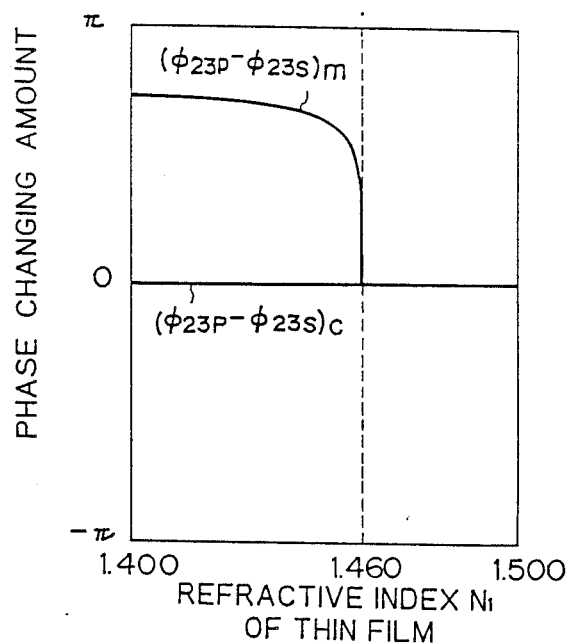

FIG. 19 shows a value ($\phi_{23P} - \phi_{23S}$)$_c$ and a measured value ($\phi_{23P} - \phi_{23S}$)$_m$ calculated when this refractive index is calculated.

On the basis of the difference between the phase changing amounts of the P-polarized light and the S-polarized light on the boundary face between the thin film and the substrate, the value ($\phi_{23P} - \phi_{23S}$)$_c$ is calculated by using the measured Rp and Rs and the value ($\phi_{23P} - \phi_{23S}$)$_m$ is calculated by using the known refractive indexes of the substrate and the incident medium. The refractive index of the thin film is changed in a range from 1.400 to 1.500.

In the PRETTI method, the accuracy in measurement of the refractive index increases as the values ($\phi_{23P} - \phi_{23S}$)$_c$ and ($\phi_{23P} - \phi_{23S}$)$_m$ clearly cross each other. FIG. 19 clearly shows such a state and therefore the accuracy in measurement of the refractive index obtained as above is high.

Figure 20:
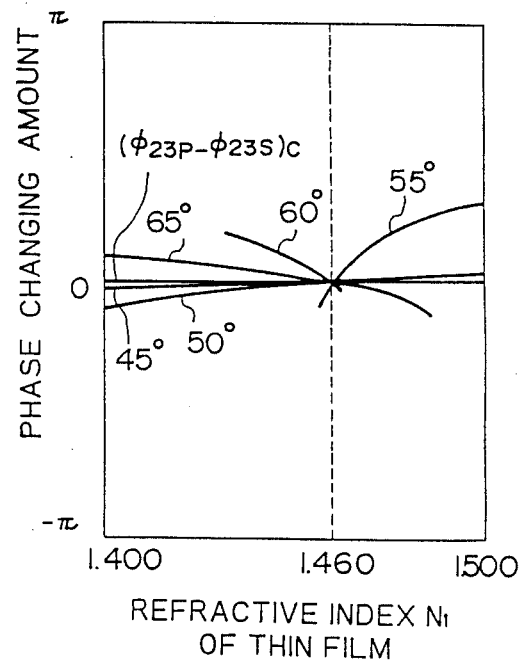

For comparison, FIG. 20 shows the $(\phi_{23P}-\phi_{23S})_c$ when the measured incident angle is set to 45 degrees, 50 degrees, 55 degrees, 60 degrees and 65 degrees, and each $(\phi_{23P}-\phi_{23S})_m$. Each $(\phi_{23P}-\phi_{23S})_m$ is distinguished by the incident angle. The $(\phi_{23P}-\phi_{23S})_c$ is not almost changed by the incident angle, but each $(\phi_{23P}-\phi_{23S})_m$ is changed by the incident angle. The $(\phi_{23P}-\phi_{23S})_c$ and the $(\phi_{23P}-\phi_{23S})_m$ clearly cross each other at the incident angle in the vicinity of the Brewster angle 55.6 degrees, but unclearly cross each other as the incident angle is separated from the Brewster angle, thereby reducing the accuracy in measurement.

As mentioned above, the present invention can provide a novel method for determining the measured incident angle when the refractive index of the thin film and the film thickness are measured by the ellipsometry, the PRETTI method, etc. Since this method is constructed as above, it is possible to easily and reliably determine the measured incident angle for guaranteeing the measurement of high accuracy.

Many widely different embodiments of the present invention may be constructed without departing from the spirit and scope of the present invention. It should be understood that the present invention is not limited to the specific embodiments described in the specification, except as defined in the appended claims.

What is claimed is:

1. A method for determining a measured incident angle of a monochromatic light for measurement in the measurement of a refractive index and a thickness of a thin film of a single layer formed on a substrate having a known complex refractive index, said substrate being disposed in an incident medium having a known refractive index, said method comprising the steps of:
    measuring a first reflectance of an S-polarized light or a P-polarized light of a measured sample within said incident medium at various angles of incident of the monochromatic light having a known wavelength used in the measurement;
    calculating a second reflectance of the S-polarized light or the P-polarized light when said monochromatic light is incident to said substrate within said incident medium, said second reflectance being calculated by using said complex refractive index of said substrate and said refractive index of the incident medium as a function of the incident angle;
    calculating a first angle satisfying an equation in which the first and second reflectance are equal to each other with respect to the S-polarized light or the P-polarized light; and
    setting a second angle except for said first angle as the measured incident angle.

2. A determining method as claimed in claim 1, wherein said first reflectance of the S-polarized light or the P-polarized light is respectively represented by $Rs(\theta_0)$ or $Rp(\theta_0)$, and the second reflectance of the S-polarized light or the P-polarized light is respectively represented by $|r_{02S}(\theta_0)|^2$ or $|r_{02P}(\theta_0)|^2$.

3. A determining method as claimed in claim 2, wherein said equation is represented by the following equation, $$Rs(\theta_0) = |r_{02S}(\theta_0)|^2,$$

or $$Rp(\theta_0) = |r_{02P}(\theta_0)|^2.$$

4. A method for determining a measured incident angle of a monochromatic light for measurement in the measurement of a refractive index and a thickness of a thin film of a single layer formed on a substrate having a known complex refractive index $n^*_2 = n_2 - ik_2$, said substrate being disposed in an incident medium having a known refractive index, said method comprising the steps of:
    measuring a reflectance $Rs(\theta_0)$ or $Rp(\theta_0)$ of an S-polarized light or a P-polarized light of a measured sample within said incident medium at various angles $\theta_0$ of incident of the monochromatic light having a known wavelength $\lambda$ used in the measurement;
    calculating a reflectance $|r_{02S}(\theta_0)|^2$ or $|r_{02P}(\theta_0)|^2$ of the S-polarized light or the P-polarized light when said monochromatic light is incident to said substrate within said incident medium said reflectance $|r_{02S}(\theta_0)|^2$ or $|r_{02P}(\theta_0)|^2$ being calculated by using said refractive indexes $n^*_2$ and $n_0$ as a function of the incident angle $\theta_0$;
    calculating an angle $\theta_{a0}$ satisfying the following equation, $$Rs(\theta_0) = |r_{02S}(\theta_0)|^2,$$

or $$Rp(\theta_0) = |r_{02P}(\theta_0)|^2;$$

and
    setting an angle except for said angle $\theta_{a0}$ as the measured incident angle.

5. A method for determining a measured incident angle of a monochromatic light for measurement in the measurement of a refractive index and a thickness of a thin film formed on a base body which is composed of the thin film of more than one layer having known refractive index and thickness and stacked on a substrate having a known complex refractive index, said base body being disposed in an incident medium having a known refractive index, said method comprising the steps of:
    measuring first reflectances of an S-polarized light and a P-polarized light of a measured sample within said incident medium at various angles of incident of the monochromatic light having a known wavelength used in the measurement;
    calculating second reflectances of the S-polarized light and the P-polarized light when said monochromatic light is incident to said base body within said incident medium, said second reflectance being calculated as a function of the incident angle by using said complex refractive index of said substrate, the refractive index of the incident medium and the known refractive index and thickness of each thin film of the base body;
    calculating a first angle satisfying equations in which the first and second reflectances are equal to each other with respect to the S-polarized light and the P-polarized light; and setting a second angle except for said second angle as the measured incident angle.

6. A determining method as claimed in claim 5, wherein said first reflectance of the S-polarized light and the P-polarized light are respectively represented by $Rs(\theta_0)$ and $Rp(\theta_0)$ and said second reflectance of the S-polarized light and the P-polarized light are respectively represented by $R_{SbS}(\theta_0)$ and $R_{SbP}(\theta_0)$.

7. A determining method as claimed in claim 6, wherein said equations are represented by $$Rs(\theta_0) = R_{SbS}(\theta_0),$$

and $$Rp(\theta_0) = R_{SbP}(\theta_0).$$

8. A method for determining a measured incident angle of a monochromatic light for measurement in the measurement of a refractive index and a thickness of a thin film formed on a base body which is composed of the thin film of more than one layer having known refractive index and thickness and stacked on a substrate having a known complex refractive index $n^*_s = n_s - ik_s$, said base body being disposed in an incident medium having a known refractive index, said method comprising the steps of:

measuring reflectances $Rs(\theta_0)$ of $Rp(\theta_0)$ of an S-polarized light and a P-polarized light by a measured sample within said incident medium at various angles $\theta_0$ of incident of the monochromatic light having a known wavelength $\lambda$ used in the measurement;

calculating reflectances $R_{SbS}(\theta_0)$ and $R_{SbP}(\theta_0)$ of the S-polarized light and the P-polarized light when said monochromatic light is incident to said base body within said incident medium said second reflectances $R_{SbS}(\theta_0)$ and $R_{SbP}(\theta_0)$ being calculated as a function of the incident angle $\theta_0$ by using said refractive indexes $n^*_s$ and $n_0$ and the known refractive index and film thickness of each thin film of the base body;

calculating an angle $\theta_{a0}$ satisfying both the following equations, $$Rs(\theta_0) = R_{SbS}(\theta_0),$$

and $$Rp(\theta_0) = R_{SbP}(\theta_0);$$

and setting an angle except for said angle $\theta_{a0}$ as the measured incident angle.

9. A method for determining a measured incident angle of a monochromatic light for measurement in the measurement of a refractive index and a thickness of a thin film of a single layer formed on a substrate having a known complex refractive index, said substrate being disposed in an incident medium having a known refractive index, said method comprising the steps of:

measuring a first reflectance of a P-polarized light of a measured sample within said incident medium at various angles of incident of the monochromatic light having a known wavelength used in the measurement;

calculating a second reflectance of the P-polarized light when said monochromatic light is incident to said substrate within said incident medium, said second reflectance being calculated by using said complex refractive index of said substrate and said refractive index of said incident medium as a function of the incident angle;

calculating a first angle satisfying an equation in which the first and second reflectance are equal to each other with respect to the P-polarized light;

calculating from the values of said first angle a second angle satisfying a predetermined inequality with respect to a third angle and a fourth angle, said third angle being smaller than said first angle and proximate to said first angle, said fourth angle being greater than said first angle and proximate to said first angle; and setting said second angle or an angle proximate thereto as the measured incident angle.

10. A determining method as claimed in claim 9, wherein said first reflectance of the P-polarized light is represented by $Rp(\theta_0)$- and said second reflectance of the P-polarized light is represented by $|r_{02P}(\theta_0)|^2$.

11. A determining method as claimed in claim 10, wherein said equation is represented by $Rp(\theta_0) = |r_{02P}(\theta_0)|^2$.

12. A determining method as claimed in claim 11, wherein said third angle and said fourth are composed of angles $\theta_A$ and $\theta_C$ proximate to said first angle where the angle $\theta_A$ is smaller than the first angle and the angle $\theta_C$ is greater than the first angle.

13. A determining method as claimed in claim 12, wherein said predetermined inequality is represented by $$(Rp(\theta_A) - |r_{02P}(\theta_A)|^2) \times (Rp(\theta_C) - |r_{02P}(\theta_C)|^2) < 0.$$

14. A method for determining a measured incident angle of a monochromatic light for measurement in the measurement of a refractive index and a thickness of a thin film of a single layer formed on a substrate having a known complex refractive index $n^*_2 = n_2 - ik_2$, said substrate being disposed in an incident medium having a known refractive index no., said method comprising the steps of:

measuring a reflectance $Rp(\theta_0)$ of a P-polarized light of a measured sample within said incident medium at various angles $\theta_0$ of incident of the monochromatic light having a known wavelength $\lambda$ used in the measurement;

calculating a reflectance $|r_{02P}(\theta_0)|^2$ of the P-polarized light when said monochromatic light is incident to said substrate within said incident medium, said second reflectance $|r_{02P}(\theta_0)|^2$ being calculated by using said refractive indexes $n^*_2$ and $n_0$ as a function of the incident angle $\theta_0$;

calculating an angle $\theta_B$ satisfying the following equation, $$Rp(\theta_0) = |r_{02P}(\theta_0)|^2;$$

calculating from the values of said angle $\theta_B$ an angle $\theta_{OB}$ satisfying the following inequality, $$(R_P(\theta_A) - |r_{02P}(\theta_A)|^2) \times (R_P(\theta_C) - |r_{02P}(\theta_C)|^2) < 0;$$

with respect to angles $\theta_A$ and $\theta_C$, said angle $\theta_A$ being smaller than said angle $\theta_B$ and proximate to said angle $\theta_B$, said angle $\theta_C$ being greater than said angle $\theta_B$ and proximate to said angle $\theta_B$; and setting said angle $\theta_{OB}$ or an angle proximate thereto as the measured incident angle.

* * * * *